(12) United States Patent
Lindhofer et al.

(10) Patent No.: US 6,551,592 B2
(45) Date of Patent: *Apr. 22, 2003

(54) BI- AND TRISPECIFIC ANTIBODIES FOR THE INDUCTION OF ANTI-TUMOR IMMUNITY

(75) Inventors: Horst Lindhofer, Gröbenzell (DE); Hans-Jochem Kolb, München (DE); Stefan Thierfelder, Eichenau (DE)

(73) Assignee: GSF Forschungszentrum fur Umwelt und Gesundheit GmbH, Ingolstadter (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/923,852

(22) Filed: Sep. 3, 1997

(65) Prior Publication Data

US 2002/0051780 A1 May 2, 2002

(30) Foreign Application Priority Data

| Sep. 3, 1996 | (DE) | ......................................... | 196 35 743 |
| Nov. 26, 1996 | (DE) | ......................................... | 196 48 976 |
| Mar. 13, 1997 | (DE) | ......................................... | 196 10 497 |

(51) Int. Cl.$^7$ ............................................. A61K 39/395
(52) U.S. Cl. .............................. 424/136.1; 424/144.1; 530/387.3
(58) Field of Search .......................... 424/136.1, 130.1, 424/138.1, 144.1; 530/387.1, 387.3, 388.1, 388.8, 388.85, 388.73, 388.23

(56) References Cited

U.S. PATENT DOCUMENTS

| 4,474,893 A | 10/1984 | Reading |
| 4,954,617 A | 9/1990 | Fanger et al. |

FOREIGN PATENT DOCUMENTS

| EP | 0637593 A1 | 2/1995 |
| GB | 2 197 322 A | 5/1998 |
| WO | WO 92/05793 | 4/1992 |

OTHER PUBLICATIONS

Haagen et al. "Evaluation of Fcg receptor mediated T–cell activation by two purified CD3×CD19 bispecific monoclonal antibodies with hybrid Fc domains" Therapeutic Immunology. vol. 1. No. 5, pp. 279–287, 1994.*

Lindhofer et al. "Preferential species–restricted heavy/light chain pairing in rat/mouse quadromas" J. Immunology. vol. 145 pp. 218–225, 1995.* deGast, G. et al., "Clinical Experience with CD3×CD19 Bispecific Antibodies in Patients with B Cell Malignancies," *J. of Hematother.* 4: 433–437 (1995).

G.C. deGast, et al., *Cancer Immunol. Immunother* (1995) 40: 390–396.

G.J. Weiner, et al., *Journal of Immunology* (1994) 152: 2385–2392.

H. Lindhofer et al., "Bispecific Antobodies Target Operationally Tumor–Specific Antigens in Two Leukemia Relapse Models," *Blood* (Dec. 15, 1996) 88(12): 4651–4658.

H. Lindhofer et al., "Bispecific Antibodies Effectively Purge Cancer Cells from Peripheral Blood Stem Cell Collections without Affecting Colony Forming Units," *26th Annual Meeting of the International Society for Experimental Hematology,* Cannes, France (Aug. 24–28, 1997) 25 (8): 879.

G.J. Weiner et al., "The Role of T Cell Activation in Anti–CD3 X Antitumor Bispecific Antibody Therapy," *Journal of Immunology* (1994) 152: 2385.

G.J. Weiner et al., "Bispecific Monoclonal Antibody Therapy of B–Cell Malignancy," *Leukemia and Lymphoma* (1995) 16: 199–207.

L. M. Weiner et al., "Clinical Development of 2B1, a Bispecific Murine Monoclonal Antibody Targeting c–erB–2 and FcyRIII," *Journal of Hematotherapy* (1995) 4: 453–456.

L.M.R. Silla et al., "Potentiation of Lysis of Leukemia Cells by a Bispecific Antibody to CD33 and CD16 (FcyRIII) Expressed by Human Natural Killer (NK) Cells," *British Journal of Haematology* (1995) 89: 712–718.

J. Chen et al., "Monocyte–Mediated Lysis of Acute Myeloid Leukemia Cells in the Presence of the Bispecific Antibody 251×22 (Anti–CD33×Anti–CD64)," *Clinical Cancer Research* (Nov. 1995) 1: 1319–1325.

* cited by examiner

Primary Examiner—Sheela Huff
Assistant Examiner—Larry R. Helms
(74) Attorney, Agent, or Firm—Townsend and Townsend and Crew LLP (57) ABSTRACT

According to the invention, a method is provided wherein intact bispecific or trispecific antibodies which at the same time bind to the T cell receptor complex of a T cell, to tumor-associated antigens on a tumor cell, and, via the Fc portion of the bispecific antibody, to Fc receptor-positive cells are used for the induction of an anti-tumour immunity in humans and animals.

13 Claims, 5 Drawing Sheets

The role of accessory cells in the tumour immunotherapy by means of bispecific antibodies.

FIG. 2A Survival after injection of 5 x 10³ B16 melanoma cells and bispecific antibodies

FIG. 2B

Additional tumour injection on day 144

Fig. 3

Heterologous chimerised bispecific antibody of the isotype combination:
mouse-[VH-CH1, VL-CL]-human-IgG1-[hinge]-human-IgG1-[CH2-CH3]/
rat-[VH-CH-1, VL-CL]-human-IgG1-[hinge]-human-IgG3-[CH2-CH3]

BI- AND TRISPECIFIC ANTIBODIES FOR THE INDUCTION OF ANTI-TUMOR IMMUNITY

BACKGROUND OF THE INVENTION

The invention relates to the use of intact bispecific antibodies for the induction of anti-tumor immunity in humans and animals.

Despite of the progress in chemotherapy and radiotherapy achieved in recent years, malignant diseases in humans, for example terminal breast cancer, still have an extraordinarily unfavorable prognosis. These diseases are impossible to cure. Therefore, it is necessary to develop new treatment strategies. In this respect, great hopes are placed in immunotherapeutical approaches enabling the immune system of the patient to reject the tumor. It is well-known that tumor-associated antigens exist on tumor cells and that in principle the immune system can recognize these antigens and attack the malignant cells. Tumors have, however, developed certain strategies enabling them to escape the immune reaction for example by insufficient presentation of tumor-associated antigens and/or insufficient activation of the tumor-specific T cells which are generally present.

With about 43,000 new cases/year, breast cancer occupies a top position in the cancer statistics of women in Germany. Less than one third of the women suffering from lymph node invasion at the time of diagnosis survive for 10 years without relapse.

Against this background, attempts have been made since several years towards the prolongation of life or even healing of female patients suffering from extensive lymph node invasion and distant metastases by means of autologous bone marrow and stem cell transplantation in connection with high-dose chemotherapy. Despite high response rates to the high-dose chemotherapy a permanent cure in the metastatic stage rarely occurs.

To date, immunotherapeutic approaches to the treatment of mammary carcinoma have been restricted to methods for unspecific stimulation such as the treatment with BCG or levamisole as well as the use of LAK cells and NK cells together with IL-2. There has been no evidence for a prolongation of life by the types of immunotherapy used so far, while the treatment with BCG rather turned out to be disadvantageous. Since the unspecific activation of cells has achieved little success also with other tumor types, attempts were made to raise a specific immune reaction.

For example, T cell-redirecting bispecific antibodies have been used in tumor therapy. These antibodies are able to bind to a T cell receptor complex by one binding arm and to a tumor-specific antigen on a tumor cell by the second binding arm. Due to resulting activation of the T cell and the spatial proximity of the tumor cell, the latter is killed by either by induction of apoptosis or by cytokines such as TNF-α or perforin.

SUMMARY OF THE INVENTION

It is an object of the present invention to provide a novel method for the therapy of malignant diseases in humans.

According to the invention, this object has been achieved by the features characterized in more detail below. Preferred embodiments of the invention are obvious from the dependent claims.

Thus, the invention discloses a method for the induction of an anti-tumor immunity by administering to a human or an animal subject an efficient amount of an intact bispecific or trispecific antibody or a combination thereof, having the following properties and effects of:

(a) binding to a T cell to which it mediates a first activation signal;

(b) binding to tumor-associated antigens on a tumor cell;

(c) binding, by its Fc portion (in the case of bispecific antibodies) or a third specificity (in the case of trispecific antibodies), to the Fc receptor of Fc receptor-positive cells;

(d) activation of the Fc receptor-positive cell by binding to the Fc receptor-positive cell and, thereby, initiating or increasing the expression of cytokines and/or costimulatory antigens;

(e) transfer of at least a second activation signal required for physiological activation of the T cell to the T cell by the co-stimulatory antigens and/or cytokines, this activation being indicated by up-regulation of activation markers, killing of the tumor cell, and/or T cell proliferation.

Preferably, the antibodies used in the method of the present invention are able to activate the tumor-specific T cells recognizing a tumor-specific peptide presented on the tumor cells by MHC class I and/or class II via their T cell receptor upon binding to the bispecific or trispecific antibody as described under (e).

Further, the antibodies used according to the invention are able to reactivate the tumor-specific T cells being in an anergic state. Furthermore, they are able to induce tumor-reactive complement-binding antibodies and, thus, induce a humoral immune reaction.

Binding to the T cell takes place via CD3, CD2, CD5, CD28, and/or CD44. The Fc receptor-positive cells have at least one Fcγ receptor I, II, or III.

The antibody used according to the invention is able to bind to monocytes, macrophages, and/or dendritic cells being Fcγ receptor I-positive cells.

The antibodies used according to the invention lead to the initiation or increase of the expression of CD40, CD80, CD86, ICAM-1, and/or LFA-3 being co-stimulatory antigens and/or secretion of cytokines by the Fc receptor-positive cell. Preferably, the cytokines are IL-1, IL-2, IL-4, IL-6, IL-8, IL-12, and/or TNF-α.

Preferably, binding to the T cell takes place via the T cell receptor complex of the T cell.

The bispecific antibody used in the invention preferably is an anti-CD3 X anti-tumor-associated antigen antibody and/or anti-CD2 X anti-tumor-associated antigen antibody and/or anti-CD5 X anti-tumor-associated antigen antibody and/or anti-CD28 X anti-tumor-associated antigen antibody and/or anti-CD44 X anti-tumor-associated antigen antibody.

The trispecific antibody used according to the invention preferably is an anti-CD3 X anti-tumor-associated antigen antibody and/or anti-CD2 X anti-tumor-associated antigen antibody and/or anti-CD5 X anti-tumor-associated antigen antibody and/or anti-CD28 X anti-tumor-associated antigen antibody and/or anti-CD44 X anti-tumor-associated antigen antibody having an additional anti-Fc receptor binding arm.

Regarding feature (a), the first signal is for example transduced via the T cell receptor complex of the T cell and, therefore, may itself lead to an unphysiological T cell activation. By this, the cell is anergized and unable to react to T cell receptor-mediated stimuli. In addition, a second activation signal is transduced simultaneously to the T cell by the bispecific or trispecific antibodies of the invention via the co-stimulatory antigens on the Fc receptor-positive cell which causes physiological activation of the T cell and, subsequently, leads to killing of the tumor cell and/or proliferation of the T cell. As a further criterion for T cell activation the up-regulation of cell surface antigens such as CD2, CD25, and/or CD28, and/or the secretion of cytokines such as IL-2 may be used.

Thus, by the use of the bsAb described according to the invention T cells are activated and retargeted against the tumor cells. Generally, the use of an unspecific activation of T cells has been of little success in immune therapy.

Preferred antibodies are heterologous bispecific antibodies selected of one or more of the following combinations of isotypes:

rat-IgG2b/mouse-IgG2a,
rat-IgG2b/mouse-IgG2b,
rat-IgG2b/mouse-IgG3;
rat-IgG2b/human-IgG1,
rat-IgG2b/human-IgG2,
rat-IgG2b/human-IgG3 [oriental allotype G3m(st)= binding to protein A],
rat-IgG2b/human-IgG4;
rat-IgG2b/rat-IgG2c;
mouse-IgG2a/human-IgG3 [caucasian allotypes G3m(b+g)=no binding to protein A, in the following indicated as *]
mouse-IgG2a/mouse-[VH-CH1, VL-CL]-human-IgG1-[hinge]-human-IgG3*-[CH2-CH3]
mouse-IgG2a/rat-[VH-CH1, VL-CL]-human-IgG1-[hinge]-human-IgG3*-[CH2-CH3]
mouse-IgG2a/human-[VH-CH1, VL-CL]-human-IgG1-[hinge]-human-IgG3*-[CH2-CH3]
mouse-[VH-CH1, VL-CL]-human-IgG1/rat-[VH-CH1, VL-CL]-human-IgG1-[hinge]-human-IgG3*-[CH2-CH3]
mouse-[VH-CH1, VL-CL]-human-IgG4/rat-[VH-CH1, VL-CL]-human-IgG4-[hinge]-human-IgG4 [N-terminal region of CH2]-human-IgG3*[C-terminal region of CH2:>aa position 251]-human-IgG3*[CH3]
rat-IgG2b/mouse-[VH-CH1, VL-CL]-human-IgG1-[hinge-CH2-CH3]
rat-IgG2b/mouse-[VH-CH1, VL-CL]-human-IgG2-[hinge-CH2-CH3]
rat-IgG2b/mouse-[VH-CH1, VL-CL]-human-IgG3-[hinge-CH2-CH3, oriental allotype]
rat-IgG2b/mouse-[VH-CH1, VL-CL]-human-IgG4-[hinge-CH2-CH3]
human-IgG1/human-[VH-CH1, VL-CL]-human-IgG1-[hinge]-human-IgG3*-[CH2-CH3]
human-IgG1/rat-[VH-CH1, VL-CL]-human-IgG1-[hinge]-human-IgG4 [N-terminal region of CH2]-human-IgG3*[C-terminal region of CH2:>aa position 251]-human-IgG3*[CH3]
human-IgG1/mouse-[VH-CH1, VL-CL]-human-IgG1-[hinge]-human-IgG4 [N-terminal region of CH2]-human-IgG3*[C-terminal region of CH2:>aa position 251]-human-IgG3*[CH3]
human-IgG1/rat-[VH-CH1, VL-CL]-human-IgG1-[hinge]-human-IgG2 [N-terminal region of CH2]-human-IgG3*[C-terminal region of CH2:>aa position 251]-human-IgG3*[CH3]
human-IgG1/mouse-[VH-CH1, VL-CL]-human-IgG1-[hinge]-human-IgG2 [N-terminal region of CH2]-human-IgG3*[C-terminal region of CH2:>aa position 251]-human-IgG3*[CH3]
human-IgG1/rat-[VH-CH1, VL-CL]-human-IgG1-[hinge]-human-IgG3*-[CH2-CH3]
human-IgG1/mouse-[VH-CH1, VL-CL]-human-IgG1-[hinge]-human-IgG3*-[CH2-CH3]
human-IgG2/human-[VH-CH1, VL-CL]-human-IgG2-[hinge]-human-IgG3*-[CH2-CH3]
human-IgG4/human-[VH-CH1, VL-CL]-human-IgG4-[hinge]-human-IgG3*-[CH2-CH3]
human-IgG4/human-[VH-CH1, VL-CL]-human-IgG4-[hinge]-human-IgG4 [N-terminal region of CH2]-human-IgG3*[C-terminal region of CH2:>aa position 251]-human-IgG3*[CH3]
mouse-IgG2b/rat-[VH-CH1, VL-CL]-human-IgG1-[hinge]-human-IgG3*-[CH2-CH3]
mouse-IgG2b/human-[VH-CH1, VL-CL]-human-IgG1-[hinge]-human-IgG3*-[CH2-CH3]
mouse-IgG2b/mouse-[VH-CH1, VL-CL]-human-IgG1-[hinge]-human-IgG3*-[CH2-CH3]

BRIEF DESCRIPTION OF THE DRAWINGS

The invention will be illustrated in more detail by means of the accompanying Figures. The Figures show.

DESCRIPTION OF THE PREFERRED EMBODIMENTS

The object of the invention aims to induction of an anti-tumor immunity and in particular a long-lasting anti-tumor immunity by raising an efficient T cell response against tumor cells. This object has been achieved by redirection of T cells to tumor cells by means of intact bispecific antibodies (bsAb) and concomitant binding of Fc receptor-positive cells to the Fc portion of the bsAb. In this respect, it is important to note that the Fc receptor-positive cell is activated by binding of immobilized intact bsAb (at the T cell or tumor cell, respectively) to the Fc receptor. "Long-lasting anti-tumor immunity" according to the invention is meant to be a period of time spanning at least several years.

The bispecific and trispecific antibodies described in the method of the present invention are characterized in particular by the features described in the claims and preferably of course by the features (a)–(e) described on page 2. Thus, these antibodies may be used for the induction of an anti-tumor immunity, preferably a long-lasting anti-tumor immunity in humans and animals which will be particularly caused by features described under items (a)–(e) on page 2.

Preferably, specific subclasses or combinations of subclasses, respectively, of the bsAb or in the case of trispecific antibodies a binding arm recognizing the Fc receptor are employed for the activation of the Fc receptor-positive cell by the bsAb. For example, in vitro experiments showed that bsAb of the mouse-IgG2a/rat-IgG2b subclass combination are able to bind to and simultaneously activate Fc receptor-positive cells leading to up-regulation or new formation (expression), respectively, of co-stimulatory antigens such as CD40, CD80, or CD86 on the surface of these cells, whereas bsAb of the mouse-IgG1/rat-IgG2b subclass combination are able to bind to Fc receptor-positive cells (Haagen et al., Interaction of human monocyte Fcγ receptors with rat IgG2b, J. Immunology, 1995, 154:1852–1860) but obviously are unable to activate these cells to a comparable extent (Gast G. C., Haagen I. -A., van Houten A. A., Klein S., Duits A. J., de Weger R. A., Vroom T. M., Clark M. R., J. Phillips, van Dijk A. J. G., de Lau W. B. M., Bast B. J. E. G. CD8 T-cell activation after intravenous administration of CD3×CD19 bispecific antibody in patients with non-Hodgkin lymphoma. Cancer Immunol. Immunother. 40:390, 1995)

Figure 1A:
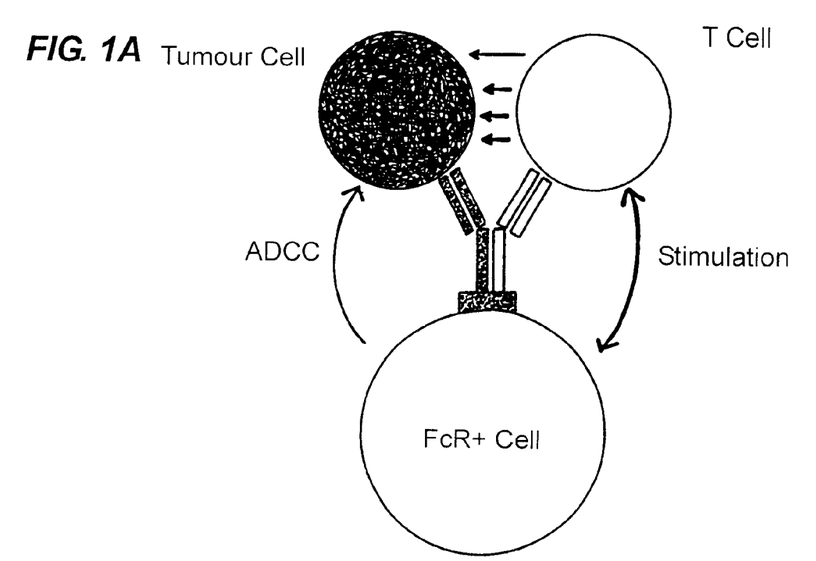
FIG. 1a: The role of accessory cells including T cells in the immune therapy of tumors using bispecific antibodies.

While the intact bsAb binds to the T cell with one binding arm (e.g. CD3 or CD2) and activates it at the same time, co-stimulatory signals from the Fc receptor-positive cell bound to the Fc portion of the bsAb can be transferred to the T cell. That means, only the combination of T cell activation via one binding arm of the bsAb and simultaneous mediation of co-stimulatory signals from the Fc receptor-positive cell to the T cell leads to efficient T cell activation (FIG. 1A).

Also, tumor-specific T cells which have been insufficiently activated at the tumor cell site and, therefore, remain in an anergic state may be reactivated by the principle of the invention described above (FIG. 1B).

Thus, surprisingly by the inventive use of intact T cell-redirecting bsAb a long-lasting anti-tumor immunity could be induced according to the invention. This was based on the physiological activation of tumor-retargeted T cells by 1) binding of the bsAb to the T cell, for example via the T cell receptor complex, and 2) simultaneous transfer of co-stimulatory signals by FcR+ cells binding to the Fc portion of the bsAb.

Thus, an important prerequisite for an efficient induction of anti-tumor immunity is the use of bsAbs having a Fc portion able to bind to FcR+ cells which are activated themselves by this event and, thereby, able to mediate co-stimulatory signals to the T cell.

Due to this mechanism, tumor-specific anergic T cells (having a T cell receptor [TCR] which recognizes tumor-specific peptides in association with MHC molecules on the tumor cell) can be reactivated at the tumor cell site, and thereby, the tumor tolerance can be reversed.

Since the tumor-specific T cells via their TCR are able to recognize completely different peptides/proteins than the bsAb via its anti-tumor binding arm, additional tumor cells may be recognized and killed after activation of such T cells by the bsAb which have initially not been recognized by the bsAb. That means, it is not neccessary for the bsAb used to recognize all of the tumor cells to induce an anti-tumor immunity which afterwards includes all of the tumor cells. A further conclusion to be drawn from this knowledge is that a relatively low amount of intact bsAb (100 μg–5 mg/patient) is sufficient to achieve the anti-tumor immunity of the invention. Since induction of such an anti-tumor immunity takes some time the patient should be in a minimal residual disease (MRD) situation with a low amount of residual tumor cells at the start of therapy. MRD is intended to mean the period of time after reduction of larger tumor portions using suitable methods such as surgical measures for removal of the primary tumor during which residual tumor cells still exist which possibly may not be detected but after some time may lead to recurrence.

This has the following advantages for the type of therapy described herein:

The number of tumor cells and, thus, the possible appearance of so-called "escape mutants", i.e. for example of tumor variations no longer presenting a tumor-specific peptide recognized by the immune system, is strongly reduced.

After "immunization" has taken place even very fast-growing and aggressive tumor variations are less apt to more or less overrun the immune system.

The main differences compared to conventional cancer therapy using bsAb are 1. the lower amount of antibody administered (5 μg–10 mg, preferably 10 μg–100 μg, further 100 μg–5 mg/patient); and
2. the time of administration of the bsAb with respect to the stage of the disease (preferably in a MRD situation). This type of therapy does not wait until tumor cells are again detectable, for example after removal of a primary tumor, but instead by the administration of intact bsAb a kind of preventive immunization of the patient against his own cancer cells is carried out;
3. this is possible because with such low amounts of intact bsAb administered no severe side effects have to be expected which would neutralize the enormous advantage—namely the absence of metastases impossible to cure;
4. the induction of a humoral immune reaction accompanied by complement-fixing antibodies (isotypes IgG1, IgG2, and IgG3 in humans) able to kill tumor cells.

Preferably, the antibodies according to the invention are monoclonal, chimeric, recombinant, synthetic, semi-synthetic, or chemically modified intact antibodies having for example Fv, Fab, scFv, or F (ab)$_2$ fragments.

If the antibodies used in the method of the present invention shall be used in an in vivo therapy, preferably antibodies or derivatives or fragments of human origin are used, or antibodies modified to be suitable for the use in humans (so-called "humanized antibodies") (see for example Shalaby et al., J. Exp. Med. 175 (1992), 217; Mocikat et al., Transplantation 57 (1994), 405).

The preparation of the different types of antibodies and antibody fragments mentioned above is obvious to the skilled artisan. The preparation of monoclonal antibodies preferably of mammalian origin, e.g. of human, rat, mouse, rabbit, or goat, can be performed using conventional methods for example as those described in Köhler and Milstein (Nature 256 (1975), 495), in Harlow and Lane (Antibodies, A Laboratory Manual (1988), Cold Spring Harbor) or in Galfré (Meth. Enzymol. 73 (1981), 3).

It is further possible to prepare the antibodies described by means of recombinant DNA technology according to techniques obvious to the skilled artisan (see Kurucz et al., J. Immunol. 154 (1995), 4576; Hollinger et al., Proc. Natl. Acad. Sci. USA 90 (1993), 6444).

The preparation of antibodies having two different specificities, the so-called bispecific antibodies, can be performed for example using recombinant DNA technology but also by the so-called hybrid hybridoma fusion technique (see for example Milstein et al., Nature 305 (1983), 537). This technique consists of fusing hybridoma cell lines each producing antibodies having one of the desired specificities and identifying and isolating recombinant cell lines producing antibodies having both specificities.

The problem forming the basis of the invention can be overcome using either bispecific or trispecific antibodies if they exhibit the properties and effects characterized on pages 2–5.

The preparation of antibodies exhibiting three specificities, so-called trispecific antibodies, also suitable to solve the basic problem of the invention may for example be carried out by coupling a third antigen binding site having an additional specificity, e.g. in the form of "single chain variable fragments" (scFv) to one of the IgG heavy chains of a bispecific antibody. The scFv may be coupled for example using a-S-S($G_4S$)$_n$D-I(SEQ ID NO:1)linker to one of the heavy chains (S=serine, G=glycine, D=aspartate, I=isoleucine).

Figure 4:
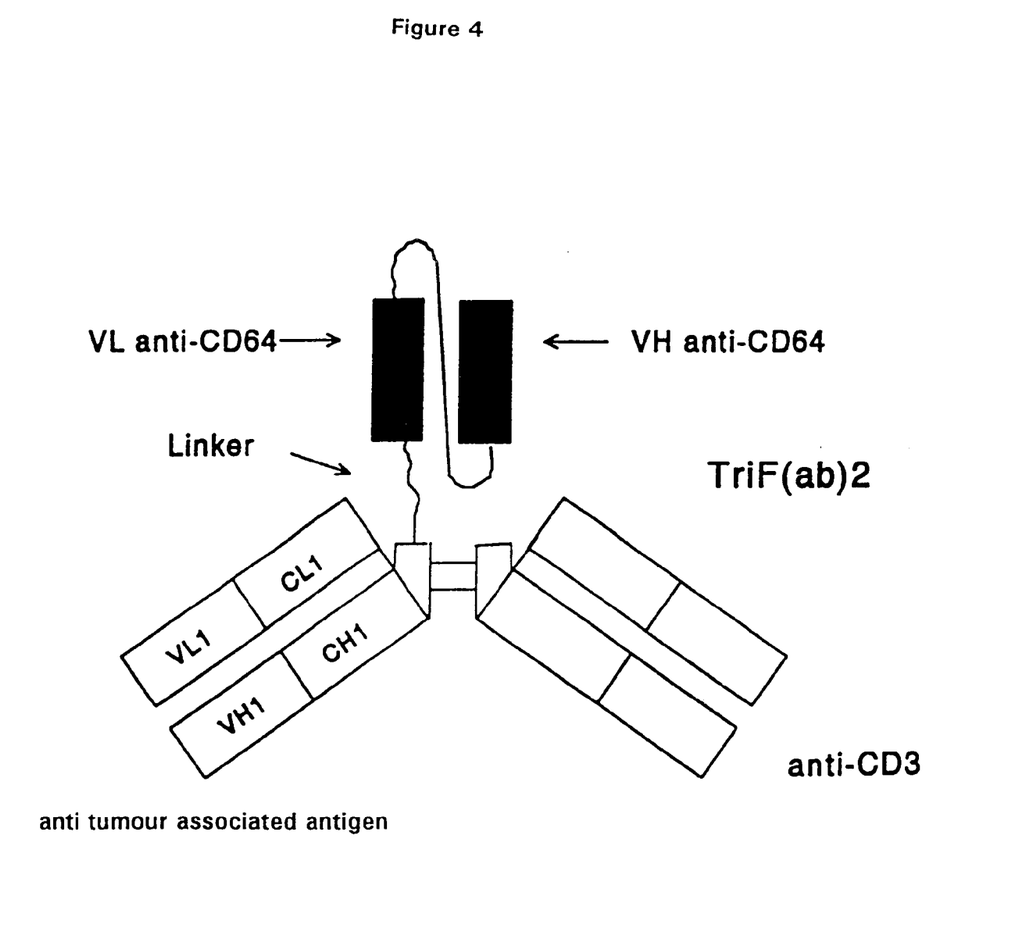
FIG. 4: trispecific F(ab)$_2$ antibody.

Analogously, trispecific F(ab)$_2$ constructs may be prepared by replacing the CH2-CH3 regions of the heavy chain of one specificity of a bispecific antibody by an scFv having a third specificity, while the CH2-CH3 regions of the heavy chain having the other specificity can be removed for example by insertion of a stop codon (at the end of the "hinge" 5 region) into the coding gene, e.g by homologous recombination (see FIG. 4).

Figure 5:
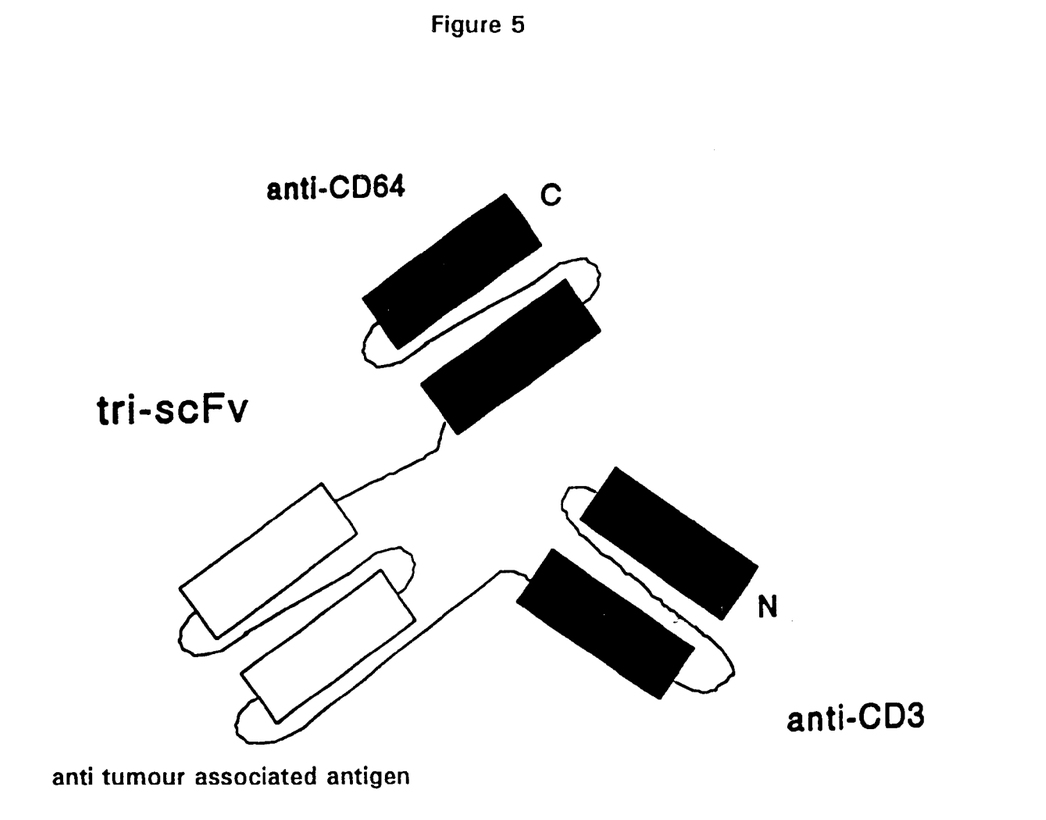
FIG. 5: trispecific scFv antibody.

It is also possible to prepare trispecific scFv constructs wherein three VH-VL regions representing three different specificities are arranged in series (FIG. 5).

According to the invention there are for example used intact bispecific antibodies. Intact bispecific antibodies are composed of two antibody semi-molecules (each having a H and a L immunoglobulin chain) each representing a specificity, and additionally like normal antibodies having a Fc portion performing the well-known effector functions. They are preferably prepared using the quadroma technology. This method of preparation is exemplified in DE-A-44 19 399. For complete disclosure this document is incorporated in its entirety by reference also with respect to a definition of bispecific antibodies. It should be understood that other methods of preparation are also useful if they lead to the intact bispecific antibodies according to the above definition required according to the invention.

For example, intact bispecific antibodies may be produced in sufficient amounts using a newly developed method of preparation (Lindhofer et al., *J. Immunology*, 155:219 (1995)). The combination of two bispecific antibodies directed against two different tumor-associated antigens (e.g. c-erb-B2, ep-cam, such as GA-733-2=C215) on the mammary carcinoma cells minimizes the risk that tumor cells expressing only one of the antigens remain unidentified.

Figure 1B:
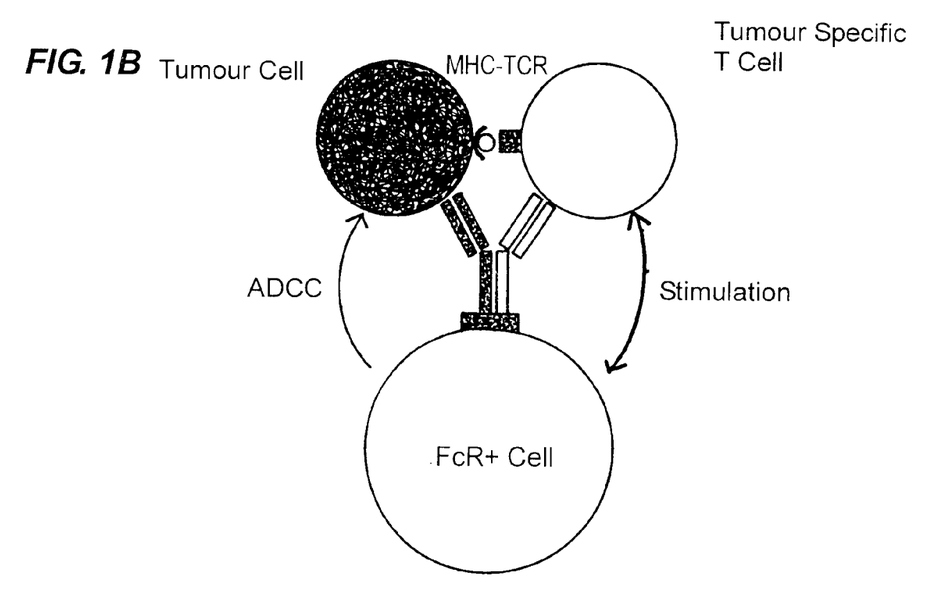
FIG. 1b: The-role of accessory cells including tumor-specific T cells in the immune therapy of tumors using bispecific antibodies.

Bispecific antibodies are able to bind to the T cell receptor complex on the T cell with one binding arm and to tumor-associated antigens on the tumor cell with the second binding arm. Thereby, T cells are activated which kill the tumor cells by releasing cytokines or by apoptosis-mediating mechanisms. In addition, there is the possibility that T cells recognize tumor-specific antigens by their receptor during activation by the bispecific antibodies and, thereby, a long-lasting immunization is initiated (FIG. 1B). Of particular importance in this respect is the intact Fc portion of the bispecific antibody which mediates the binding to accessory cells such as monocytes/macrophages/dendritic cells and causes these cells to develop cytotoxicity, and/or concomitantly transfer important co-stimulatory signals to the T cell (FIG. 1).

In this manner, a T cell reaction may also be induced against tumor-specific peptides which are unknown to date.

By redirection of possibly anergized tumor-specific T cells to tumor cells by the bsAb and concurrent co-stimulation of such cells by accessory cells binding to the Fc portion of the bsAb the anergic state of the CTLs may be reversed. I.e. according to the invention a preexisting T cell tolerance in the patient against the tumor is reversed by means of intact bsAb and, thus, a long-lasting anti-tumor immunity is induced.

This is supported by initial in vivo data from experiments with mice pointing to such a long-lasting anti-tumor immunity after treatment with a syngeneic tumor and intact bsAb. In these experiments, 14 out of 14 test animals which were successfully treated with bsAb following a first tumor injection survived a further tumor injection carried out 144 days after the first injection—without additional administration of bsAb (see Example 1).

The immunization strategy according to the invention uses for example intact bsAb able to bind to FcγRI+ cells via their Fc portion. In addition, the bsAb used according to the invention have as a second specificity besides the tumor cell-binding specificity for example anti-CD3, i.e. they are able to bind to T cells via the second binding arm. Thus, by the bsAb used according to the invention T cells are activated and redirected against the tumor cells.

It has been attempted to achieve anti-tumor immunity by treatment with bispecific F(ab')2 fragments having the specificities anti-c-erb-B2 x anti-CD64. The main disadvantage of bsF(ab')2 fragments is that due to the specificities used merely FcγRI+ cells are redirected to the tumor. T cells are not redirected to the tumor by this bispecific antibody. The bsF(ab')2 fragments have the potential to directly kill the tumor but themselves are not able to establish anti-tumor immunity. Only the T cell with its specific T cell receptor is able to confer anti-tumor immunity. The FcγRI+ cells are able to indirectly activate tumor-specific T cells by presentation of tumor-specific peptides (via MHC I or MHC II, respectively) for example after phagocytosis of tumor cell components but the efficiency of induction of anti-tumor immunity in this case is not as high (only in 30% of patients).

Further advantages of intact bsAb able to redirect T cells compared to the above-mentioned bsF(ab')2 fragments are detailed as follows:

1. It is possible for Fc receptor-positive cells to bind to intact bsAb and on the one hand to contribute directly to tumor killing via ADCC (antibody-dependent cell-mediated cytotoxicity) and on the other hand contribute to T cell activation as detailed above.
2. The circulation time of bsAb with Fc portion is significantly longer than for example of bsF(ab')2 or bs(scFv) antibody fragments so that considerably lower doses of intact ab molecules are required to achieve a comparable anti-tumor effect.
3. The use according to the invention of intact bispecific antibodies is in particular directed to the killing of residual tumor cells/micrometastases. In contrast to the treatment of solid tumors or larger metastases in which the above-mentioned antibody fragments may be advantageous since they allow for better penetration of the tumor due to their smaller size.
4. Intact T cell-redirecting bsAb function also in directing anergized tumor-specific T cells to the tumor cell which according to the invention may be reactivated directly at the tumor site. This is impossible to achieve using a bsF(ab')2 fragment having the specificities anti-CD64 X anti-tumor-associated antigen.
5. A bsF(ab')2 fragment having the specificities anti-CD64 X anti-tumor-associated antigen is only able to achieve anti-tumor immunity in 30% of the patients while according to the invention in experiments with mice a protection of 100% of the animals could be achieved using T cell-redirecting intact bsAb.

The binding of bsAb to Fcγ-RI shows two essential advantages with regard to an optimal anti-tumor effectivity: Fc-γ-RI-positive cells have the ability to eliminate tumor cells by ADCC (Valerius et al., *Blood*, 82:931–939 (1993)) and, thus, are able to contribute synergistically to the anti-tumor effect of the cytotoxic T cells directed to the tumor by the bsAb (Weiner et al., *J. Immunology*, 152:2385 (1994)).

1. FcγRI-positive cells (such as monocytes/macrophages/dendritic cells) are able to provide important co-stimulatory signals similar to antigen presentation to the T cell and, thereby, prevent anergizing of the T cell. Furthermore, as shown in FIG. 1, even T cells having a T cell receptor which recognizes tumor-specific peptides (presented via MHC antigens on the tumor cell) can be stimulated as a desired by-product due to the bsAb-mediated interaction of the T cell with accessory cell and tumor cell. In this constellation, the co-stimuli necessary for correct activation of the T cell would be provided by the accessory cell (such as the monocyte). Thus, besides the direct T cell receptor-independent bsAb-mediated tumor killing (FIG. 1A) the solution of the invention should also be able to activate and generate tumor-specific T cells (FIG. 1B) which after degradation of the bsAb continue to patrol in the patient. That means, similar to genetherapeutic approaches (e.g. by incorporation of co-stimulatory antigens such as B-7 in the tumor cell) by intact bsAb the tumor tolerance in the patient can be reversed.

In this respect it is further advantageous that the expression of Fcγ-RI on the respective cells is up-regulated after G-CSF treatment.

EXAMPLE

Figure 2A:
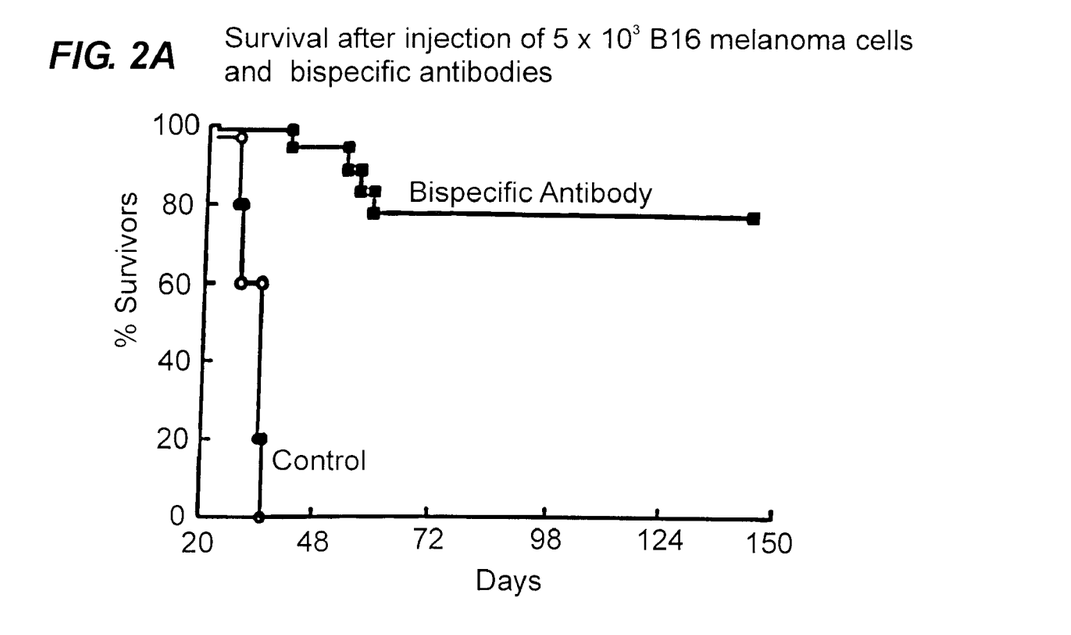
FIG. 2a: A diagram of the results obtained in the in vivo experiment after a first injection.
Figure 2B:
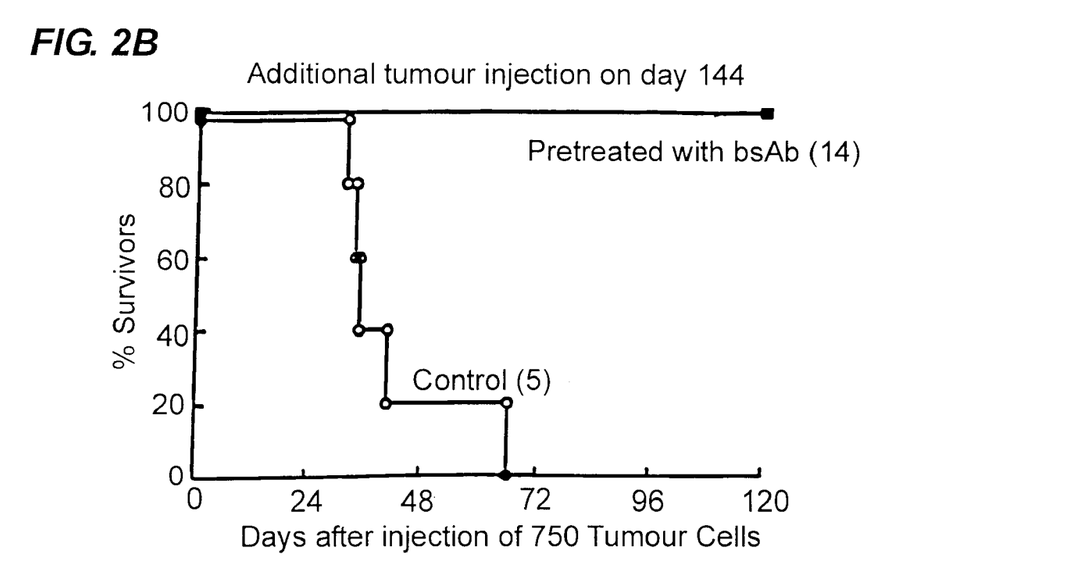
FIG. 2b: A diagram of the results obtained in the in vivo experiment after a second injection.
Figure 3:
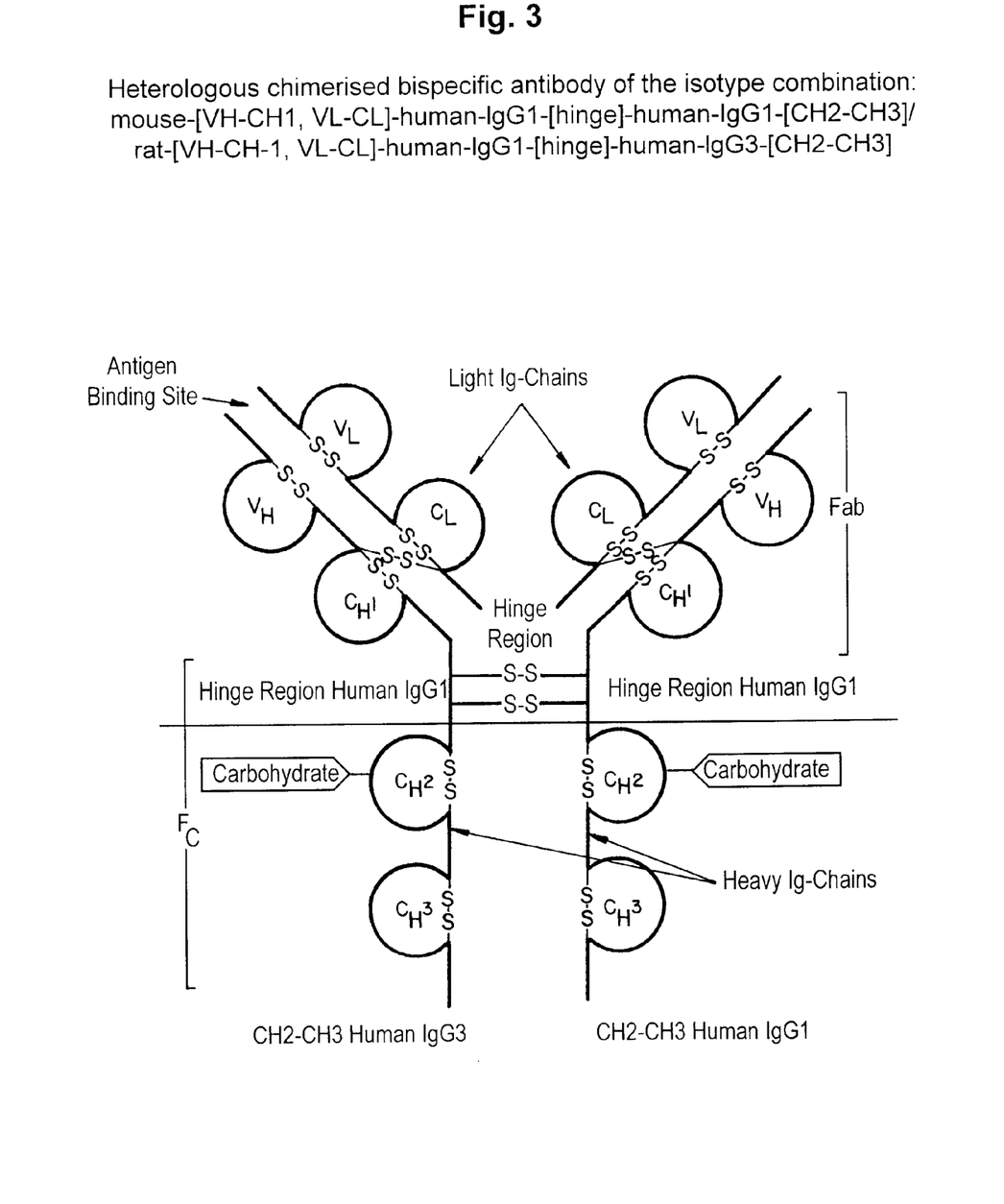
FIG. 3: an example of a bispecific antibody according to the invention.

To investigate the question of induction of an anti-tumor immunity by bispecific antibodies C57BL/6 mice were first injected with $5 \times 10^3$ syngeneic B16 tumor cells. Two days later, one group of mice (n=18) was treated with an intact bsAb prepared using quadroma technology (Lindhofer et al., *J. Immunology*, 155:219 (1995)) and which recognizes an epCAM target structure (C215=tumor-associated antigen) on the tumor cell as well as CD3 on T cells. This bsAb was of the IgG2a/rat IgG2b subclass combination. A second group (n=6) only received an equimolar amount of Fab fragments of the two specificities contained in the bsAb. While all of the animals of the Fab control group died within 56 days or had to be put to sleep, 14 out of the 18 animals treated with bsAb survived. The surviving animals received an i.p. injection of an additional dose of 750 B16 tumor cells 144 days after the first injection of tumor cells but this time without administration of bsAb. The same amount of tumor cells was administered to five untreated animals serving as a control. While the last animal of the untreated control group had to be put to sleep 66 days after tumor injection, all of the animals treated with bsAb survived (monitoring period: 120 days after second injection of tumor cells). See also FIGS. 2A and 2B: Survival curves of the two successive experiments described above.

These experiments show that it is possible to induce a long-lasting anti-tumor immunity using the bispecific antibodies and also the trispecific antibodies provided according to the invention. It can be expected that these events may also be applied to humans in which case a long-term anti-tumor immunity lasting at least several years can be expected.

Detection of the Induction of a Humoral Immune Reaction by Intact bsAb and the Importance thereof for the Prognosis of the Survival of Patients or Animals Description:

Besides the cellular immunity mainly kept up by the T cells the humoral immunity plays a similar important role in tumor recognition and killing. Evidence for this comes from a number of investigations, for example the work of Rodolfo et al. (J. Immunol. 157, 5536, 1996). Rodolfo et al. were able to show that (1) tumor-specific T cells are induced by administration of tumor cell vaccine transduced by IL-12 or IL-2, respectively; (2) an effective humoral immune reaction with complement-fixing antibodies could only be generated using IL-12 transduced tumor cells. Interestingly, in these experiments only the animals survived which had developed complement-fixing antibodies with anti-tumor specificity.

By the in vitro experiments carried out according to the invention we were able to show that using the intact bispecific antibodies described herein due to their binding and activation of Fcγ receptor-positive cells (see FIG. 1) the latter were able to generate and secrete cytokines such as IL-12 (see Annex Table 1). Thus, by the intact bsAb described herein it was possible to induce the production of cytokines without gene transfer which otherwise can only be expressed using gene transfer in the framework of gene therapeutic approaches. This observation is of importance because IL-12 obviously plays an important role in the induction of an anti-tumor immunity.

In the animal experiments shown in the Example described above tumor-reactive complement-fixing antibodies could be detected in tail blood of the surviving mice after bsAb treatment on day 143 after tumor administration. This shows that such antibodies at least contributed to the survival of the animals since in the deceased animals no or only low amounts of these antibodies could be detected.

The experiments described above were performed using bispecific antibodies. Instead of the bispecific antibodies, it is also possible to use the trispecific antibodies described in the specification to obtain similar results.

As described, by treatment with the bispecific and trispecific antibodies provided according to the invention tumor-reactive complement-binding antibodies are generated being indicative for the induction of a humoral immune reaction. This together with the induction of the production of cytokines such as IL-12 probably at least contributes to the induction of long-term anti-tumor immunity according to the invention. Therefore, it is also possible to use the amount of complement-binding tumor-reactive antibodies induced by the treatment with bispecific or trispecific antibodies according to the invention for the assessment of the course of the disease (prognosis) of a tumor patient. The higher the amount of tumor-reactive complement-fixing antibodies, the more favorable is the prognosis of the tumor patient.

The use of for example intact bispecific antibodies disclosed according to the invention is carried out after treatment of a primary tumor, preferably in patients being in a minimal residual disease (MRD) situation. The use of intact bispecific antibodies according to the invention will only gain importance in patients having a low amount of residual tumor cells but with a high risk of recurrence.

The term "tumor immunity" comprises the induction for a humoral and/or cellular immunity directed against the tumor of a human or animal suffering from tumor disease. This means that tumor specific antibodies and/or tumor specific T cells or other immune cells are induced which are directed against the tumor.

TABLE 1

Increase in surface antigens on CD14+ cells (macrophages, monocytes) or secretion of cytokines, respectively, after in vitro incubation of PMBC with intact bsAb and tumor cells after 20 h.

| Antigen | without ab | with bsAb |
|---|---|---|
| CD40 | + | ++ |
| CD80 (B-7.1) | + | ++ |
| CD86 (B-7.2) | + | ++ |
| CD25 (IL-2R) | + | +++ |
| MHC II | + | +(+) |
| bsAb | − | + |

Cytokines detected by PCR: IL-1, IL-2, IL-4, IL-6, IL-12 (only with bsAb), TNF-α (with bsAb and with a combination of parental antibodies)

References

1. Lindhofer et al, Preferential species-restricted heavy-light chain pairing in rat-mouse quadromas: Implications for a single step purification of bispecific antibodies, *J. Immunology* 1995, 155:219
2. Valerius et al., Involvement of the high-affinity receptor for IgG (FcγRI; CD64) in enhanced tumor cell cytotoxicity of neutrophils during granulocyte colony-stimulating factor therapy, *Blood*, 1993, 82:931–939
3. Weiner et al., The role of T cell activation in anti-CD3 x antitumor bispecific antibody therapy, *J. Immunology*, 1994, 152:2385 rat-IgG2b/mouse-IgG2b,
rat-IgG2b/mouse-IgG3,
rat-IgG2b/human-IgG1,
rat-IgG2b/human-IgG2,
rat-IgG2b/human-IgG3(oriental allotype G3m(st)= binding to protein A),
rat-IgG2b/human-IgG4,
rat-IgG2b/rat-IgG2c,
mouse-IgG2a/human-IgG3(caucasian allotypes G3m(b+ g)=no binding to protein A),
mouse-IgG2a/mouse-(VH-CH1,VL-CL)-human-IgG1-(hinge)-human-IgG3 Caucasian allotypes G3m(b+g)= no binding to protein A-(CH2-CH3),
mouse-IgG2a/rat-(VH-CH1,VL-CL)-human-IgG1-(hinge)-human-IgG3 caucasian allotypes G3m(b+g)= no binding to protein A-(CH2-CH3),
mouse-IgG2a/human-(VH-CH1,VL-CL)-human-IgG1-(hinge)-human IgG3 caucasian allotypes G3m(b+g)= no binding to protein A-(CH2-CH3),
mouse-(VH-CH1,VL-CL)-human-IgG1/rat-(VH-CH1, VL-CL)-human-IgG1-(hinge)-human-IgG3 caucasian allotypes G3m(b+g)=no binding to protein A-(CH2-CH3),
mouse-(VH-CH1,VL-CL)-human-IgG4/rat-(VH-CH1, VL-CL)-human-IgG4-(hinge)-human-IgG4(N-terminal region of CH2)-human-IgG3 caucasian allotypes G3m(b+g)=no binding to protein A (C-terminal region of CH2:>aa position 251)-human-IgG3 caucasian allotypes G3m(b+g)=no binding to protein A (CH3),

What is claimed is:

1. A method of treatment of a human or animal subject suffering from a tumor disease consisting of administering to said subject an effective amount of an intact heterologous bispecific antibody having isotype combinations selected from the group consisting of:
    rat-IgG2b/mouse-IgG2a,
    rat-IgG2b/mouse-(VH-CH1,VL-CL)-human-IgG1-(hinge-CH2-CH3),
    rat-IgG2b/mouse-(VH-CH1,VL-CL)-human-IgG3-(hinge-CH2-CH3, oriental allotype),
    rat-IgG2b/mouse-(VH-CH1,VL-CL)-human-IgG4-(hinge-CH2-CH3)human-IgG1/human-(VH-CH1,VL- CL)-human-IgG1-(hinge)-human-IgG3 caucasian allotypes G3m(b+g)=no binding to protein A-(CH2-CH3), human-IgG1/rat-(VH-CH1,VL-CL)-human-IgG1-(hinge)-human-IgG4(N-terminal region of CH2)-human-IgG3 caucasian allotypes G3m(b+g)=no binding to protein A(C-terminal region of CH2:>aa position 251)-human-IgG3 Caucasian allotypes G3m(b+g)=no binding to protein A (CH3), human-IgG1/mouse-(VH-CH1,VL-CL)-human-IgG1-(hinge)-human-IgG4(N-terminal region of CH2)-human-IgG3 Caucasian allotypes G3m(b+g)=no binding to protein A(C-terminal region of CH2:>aa position 251)-human-IgG3 Caucasian allotypes G3m(b+g)=no binding to protein A (CH3), human-IgG1/rat-(VH-CH1,VL-CL)-human-IgG1-(hinge)-human-IgG2(N-terminal region of CH2)-human-IgG3 caucasian allotypes G3m(b+g)=no binding to protein A(C-terminal region of CH2:>aa position 251)-human-IgG3 caucasian allotypes G3m(b+g)=no binding to protein A (CH3), human-IgG1/mouse-(VH-CH1,VL-CL)-human-IgG1-(hinge)-human-IgG2(N-terminal region of CH2)-human-IgG3 caucasian allotypes G3m(b+g)=no binding to protein A(C-terminal region of CH2:>aa position 251)-human-IgG3 Caucasian allotypes G3m(b+g)=no binding to protein A (CH3), human-IgG1/rat-(VH-CH1,VL-CL)-human-IgG1-(hinge)-human-IgG3 caucasian allotypes G3m(b+g)= no binding to protein A-(CH2-CH3), human-IgG1/mouse-(VH-CH1,VL-CL)-human-IgG1-(hinge)-human-IgG3 caucasian allotypes G3m(b+g)= no binding to protein A-(CH2-CH3), human-IgG2/human-(VH-CH1,VL-CL)-human-IgG2-(hinge)-human-IgG3 caucasian allotypes G3m(b+g)= no binding to protein A-(CH2-CH3), human-IgG4/human-(VH-CH1,VL-CL)-human-IgG4-(hinge)-human-IgG3 caucasian allotypes G3m(b+g)= no binding to protein A-(CH2-CH3), human-IgG4/human-(VH-CH1,VL-CL)-human-IgG4-(hinge)-human-IgG4(N-terminal region of CH2)-human-IgG3 Caucasian allotypes G3m(b+g)=no binding to protein A(C-terminal region of CH2:>aa position 251)-human-IgG3 caucasian allotypes G3m(b+g)=no binding to protein A (CH3), mouse-IgG2b/rat-(VH-CH1,VL-CL)-human-IgG1-(hinge)-human-IgG3 caucasian allotypes G3m(b+g)= no binding to protein A-(CH2-CH3), mouse-IgG2b/human-(VH-CH1,VL-CL)-human-IgG1-(hinge)-human-IgG3 caucasian allotypes G3m(b+g)= no binding to protein A-(CH2-CH3), and mouse-IgG2b/mouse-(VH-CH1,VL-CL)-human-IgG1-(hinge)-human-IgG3 caucasian allotypes G3m(b+g)= no binding to protein A-(CH2-CH3);

wherein said antibody provides the following properties and effects:

(a) binding to a T cell and activating said T cell;
(b) binding to tumor-associated antigens on a tumor cell;
(c) binding, through its Fc portion to the Fc receptor of Fc receptor-positive cells;
(d) activation of said Fc receptor-positive cell by said binding of said antibodies to the Fc receptor-positive cell and, thereby initiating or increasing the expression of cytokines and/or co-stimulatory molecules;
(e) inducing a physiological activation of the T cell by a member selected from the group consisting of co-stimulatory molecules and cytokines, this activation being indicated by up-regulation of activation markers, killing of the tumor cell, T cell proliferation or a combination thereof, inducing anti-tumor immunity.

2. Method according to claim 1, wherein said antibody further is able to reactivate tumor-specific T cells, which T cells are in a state of anergy.

3. Method according to claim 2, wherein said antibody further is able to activate the tumor-specific T cells after binding to the bispecific antibody as described in (e), wherein said tumor-specific T cells recognize a tumor-specific peptide presented on the tumor cells by a member selected from the group consisting of MHC class I, MHC class II, and a combination thereof via their T cell receptor.

4. Method according to claim 1, wherein said antibody is able to induce tumor-binding complement-binding antibodies and, thereby, to induce a humoral immune response.

5. Method according to claim 1, wherein said antibody binds to the T cell via a member selected from the group consisting of CD3, CD2, CD5, CD28, and CD44.

6. Method according to claim 1, wherein said antibody is able to bind to Fc receptor-positive cells having a Fcγ receptor I, II, or III.

7. Method according to claim 6, wherein said antibody is able to bind to a member selected from the group consisting of monocytes, macrophages, and dendritic cells that are Fcγ receptor I-positive cells.

8. Method according to claim 1, wherein expression of the co-stimulatory molecules is selected from the group consisting of CD40, CD80, CD86, ICAM-1, and LFA-3 or the secretion of cytokines is initiated or increased by the Fc receptor-positive cell.

9. Method according to claim 8, wherein the cytokines are members selected from the group consisting of IL-1, IL-2, IL-4, IL-6, IL-8, IL-12, and TNF-α.

10. Method according to claim 1, wherein said binding to a T cell takes place via the T cell receptor complex of the T cell.

11. Method according to claim 1, wherein said antibody is a bi-specific antibody selected from the group consisting of anti-CD3 X anti-tumor-associated antigen antibody, anti-CD2 X anti-tumor-associated antigen antibody, anti-CD5 X anti-tumor-associated antigen antibody, anti-CD28 X anti-tumor-associated antigen antibody, and anti-CD44 X anti-tumor-associated antigen antibody.

12. Method according to claim 1, wherein said antibody is a heterologous rat/mouse bi-specific antibody.

13. Method according to claim 1, wherein said antibody is administered in an amount of 5 μg–10 mg/subject when said subject is in a minimal residual disease (MRD) situation.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 3..7
        (D) OTHER INFORMATION: /product= "OTHER"
            /note= "Gly-Gly-Gly-Gly-Ser at positions 3 through 7 may
            be repeated an unspecified number of times"

(xi) SEQUENCE DESCRIPTION: SEQ ID NO: 1:

Ser Ser Gly Gly Gly Gly Ser Asp Ile
1               5